(12) United States Patent
Sand et al.

(10) Patent No.: US 10,035,118 B2
(45) Date of Patent: Jul. 31, 2018

(54) LIPOASPIRATE STEM CELL SEPARATION SYSTEM AND METHODS THEREOF

(75) Inventors: Ted Sand, Austin, TX (US); David Chau, Sugar Land, TX (US); Matthew R. DeWitt, Georgetown, TX (US); Sujata Ghosh, Houston, TX (US); Kevin Hao-Yu Lin, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 1157 days.

(21) Appl. No.: 13/506,590

(22) Filed: Apr. 30, 2012

(65) Prior Publication Data
US 2013/0130371 A1    May 23, 2013

Related U.S. Application Data

(60) Provisional application No. 61/517,959, filed on Apr. 28, 2011.

(51) Int. Cl.
| | | |
|---|---|---|
| *A61M 5/178* | (2006.01) |
| *B01J 3/04* | (2006.01) |
| *A61B 10/02* | (2006.01) |
| *A61M 1/00* | (2006.01) |
| *A61M 5/00* | (2006.01) |
| *A61M 5/315* | (2006.01) |
| *A61M 27/00* | (2006.01) |

(52) U.S. Cl.
CPC ............. *B01J 3/04* (2013.01); *A61B 10/0283* (2013.01)

(58) Field of Classification Search
CPC .......... A61M 5/178; A61M 1/00; A61M 5/00; A61M 5/315; A61M 27/00
See application file for complete search history.

(56) References Cited

U.S. PATENT DOCUMENTS

| | | | |
|---|---|---|---|
| 7,429,488 B2 * | 9/2008 | Fraser et al. .................. | 435/366 |
| 8,808,551 B2 * | 8/2014 | Leach et al. .................. | 210/789 |
| 2005/0189283 A1 * | 9/2005 | Smit ................... | A61M 1/0056 |
| | | | 210/335 |

* cited by examiner

*Primary Examiner* — Tatyana Zalukaeva
*Assistant Examiner* — Ilya Treyger
(74) *Attorney, Agent, or Firm* — Winstead PC

(57) ABSTRACT

A system and method for isolating and separating lipoaspirate particles. The system includes a generally cylindrical container having a lid and a bottom wherein the container includes at least one input port positioned to permit a lipoaspirate fluid to enter the container above the bottom; and a source of a vacuum coupled to the container to provide a partial vacuum during use of the system.

14 Claims, 4 Drawing Sheets

LIPOASPIRATE STEM CELL SEPARATION SYSTEM AND METHODS THEREOF

This application claims priority to U.S. provisional application No. 61/517,959, filed Apr. 28, 2011, which is incorporated herein by reference.

FIELD OF THE INVENTION

This invention relates generally a lipoaspirate stem cell separation system and associated methods.

BACKGROUND OF THE INVENTION

Adipose tissue consists of an easily isolatable stroma, or a form of connective tissue from which the adult stem cells can be harvested. The stem cells specifically harvested from adipose tissue are referred to as processed lipoaspirate (PLA) cells as they are separated from other fats within the adipose tissue. These PLAs hold much hope for stem cell research as they maintain their multi-potency through adulthood. PLAs can differentiate into osteogenic, adipogenic, myogenic, and chondrogenic lineages, very much similar to mesenchymal stem cells [1]. The advantages of using adipose tissue as a source of stem cells are plentiful. Some of the major problems faced by researchers working with mesenchymal stem cells are low cell harvests, high mortality in vitro, and patient discomfort during extraction. PLAs may prove to be the answer to all of these problems. Aside from serving as a reservoir of multipotent adult stem cells, PLA's most important attribute is their similar potency to those of mesenchymal stem cells [2]. The most important use of these attributes is towards regenerative medicine and disease control. Extraction of PLAs from a patient's own fat can provide a source of stem cells that can be used for tissue regeneration that would not cause an immune response compared to cells used from other sources [3].

One of the main avenues for use of these stem cells is within regenerative medicine. In order for stem cells to fit the criteria necessary for use in regenerative medicine, they must be found in abundant quantities, harvested by a minimally invasive procedure, differentiated along multiple lineages, safely and effectively transplanted, and manufactured according to Good Manufacturing Practice guidelines. Mesenchymal stem cells are mostly separated from bone marrow extract which is a very painful process that has a very low success rate. PLAs may prove to be the answer to all of these problems. The advantages of using adipose tissue as a source of stem cells are plentiful.

Studies have also shown that along with providing more PLAs, stem cells that are isolated from lipoaspirate are also easier to grow in vitro [6]. However, the PLAs most important attribute is the fact that they are similar in potency to those of mesenchymal stem cells; they differentiate at similar rates compared to those extracted from bone marrow and show the same surface markers even when extracted from the same host [6]. The most important use of these PLAs is as a source for regenerative medicine, tissue engineering, and disease control [6]. Extraction of PLA's from a patient's own fat can provide a source of stem cells that can be used for tissue regeneration that would not generate an immune response compared to cells used from other sources [3]. For example, these multipotent cells have the potential to aid in cardiac tissue regeneration for patients with chronic heart disease [5]. In fact, PLAs can be used for the any of the potential cell lines, thus allowing for disease control treatments that lack better treatment options.

Currently, the products that are on the market concerning lipoaspirate are such that they process the tissue to separate the adipose tissue into different kinds of fat, rather than to isolate a solution of PLA's. Products that were analyzed using the 'House of Quality' technique were the Aquavage™ product, Lipivage™ product, StemSource™ product, and the traditional method of centrifugation after liposuction [4].

The Aquavage product, a product by M.D. Resource, processes the incoming flow of adipose tissue and separates emulsified fat tissue in order to transfer the fat back to the patient for reconstruction. This disposable, two liter lipoaspirate canister consists of two main inputs on the top of the canister [5]. The first opening is to the aspirator, which supplies the vacuum force, while the second input is to the cannula which delivers the fat, oil, anesthetic, and stem cell mixture. As the Aquavage product does not contain a filter of the specifications required for the separation of the stem cell mixture that is desired, use of the Aquavage to harvest stem cells would not eliminate the processing of the stem cells from the fat mixture. The Aquavage system also has a downfall in its design in that it has no damping of the incoming fluid, so the speed of the fluid causes disruption of the floating solution.

The Lipivage™ product provides a similar system but within a syringe. This product is used as a one-time fat harvesting system designed to filter intact fat cells. Its main use is to provide the plastic surgeon with a quick method to transfer fat within the patient for body resculpture [6]; however, the filter within this system fails to separate the stem cells, thus allowing them to be injected back into the body.

The StemSource product is more a process for separation rather than a complete device used on site. Currently, StemSource product is supplied with a bag in which the entire fat solution is frozen and sent to an outside lab to process. The separated stem cells are then frozen and kept in a 'bank' until further need from the patient [7]. As innovative as this method is, it does not provide a quick and efficient method of separation and processing.

Finally, the traditional method of separation, centrifugation, suffers from time needed to perform the separation and the lack of efficacy for separation. The adipose tissue must leave the operation room to another lab to get processed [7]. If the doctor wishes to cut down on time and do the centrifugation on site, there are extreme costs due to the large scale centrifuge needed.

It can be seen that all competitive products have features and drawbacks when it comes to the separation of PLAs from lipoaspirate derived during the liposuction process.

SUMMARY OF THE INVENTION

Ideally, during liposuction the device will physically separate the lipoaspirate from the heterogeneous mixture of adipose tissue collected during a liposuction. The inventors recognized the known difficulties of collecting large quantities of stem cells from currently used sources of stem cells such as bone marrow. It has been shown that adipose tissue acts as a reservoir to stems cells that are referred to as processed lipoaspirates. The current market does not provide for any in-situ processing and separation of the lipoaspirate during the surgical removal of adipose tissue. The inventors have recognized that a need exists for a portable, easy to use separation device that will involve a momentum/energy dampening system in order to sufficiently separate stem cells from lipoaspirate in the most viable method.

This invention provides a means for preliminary separation of stem cells from collected adipose tissue during lipoaspiration. The inventors recognized that there is not any preliminary method of separation, which has caused a need for an in-situ method of separation. Devices that are presently used for stem cell separation generally provide a means to separate adipose tissue for body reconstruction. In comparison, the Lipoaspirate Stem Cell Collection System of this invention provides an in-situ technique for the separation of the lipoaspirate from the heterogeneous mixture collected during liposuction.

This invention provides a solution to one or more of the problems and disadvantages discussed above.

In one embodiment, the canister of this invention comprises a cone that deflects the flow of the incoming adipose tissue mixture, a shelf that collects the larger particles of high density and low density fat, and/or a mesh to filter out the lipoaspirate from the adipose tissue mixture for separation and processing. In certain embodiments, flat shelf and slanted cone are used. Testing occurred using a surrogate to a human fat mixture, consisting of chicken fat particles in a saline solution. Pulsing created during liposuction was mimicked during testing, and it demonstrated a concern for pressure buildup at the site of incoming flow. In another embodiment, the material of the shelf is a mesh like material to allow, for the lipoaspirate continuing flowing to the bottom of the canister. In another embodiment, the invention employs an expansion chamber or lateral introduction of flow to quell the momentum of the incoming flow.

In one broad respect, this invention is a system for isolating and separating lipoaspirate particles. The system comprises a generally cylindrical container having a lid and a bottom wherein the container includes at least one input port to permit a lipoaspirate fluid to enter the container above the bottom. The input can be positioned on the lid for vertical delivery or on an inner wall of the container for lateral delivery. Preferably input is along the edge of the inner container wall. In one embodiment the input is positioned in the upper half of the container, wherein the input port is sized and adapted for lateral delivery/injection (i.e., delivered in a direction generally parallel to the bottom if the bottom is flat and at roughly a 90 degree angle to the container wall; delivered in a direction so that lipoaspirate entering the container flows circumferentially) of entering lipoaspirate fluid onto the inner wall of the container. The system includes a source of a vacuum coupled to the container to provide a partial vacuum during use of the system. Typically the vacuum source is coupled to the lid of the container. The container can include at least one exit port in the container for removing separated lipoaspirate fluid. The system can include at least one slanted shelf in the container below the input port. The system can include at least one mesh shelf in the container below the input port. Any source of vacuum is acceptable such as a mechanical vacuum that is adjustable to provide varying pressures.

In another broad respect, this invention is a method of separating lipoaspirate particles. The method comprises providing a cylindrical container having a lid and a bottom wherein the container includes at least one input port, preferably along the edge of the container wall, to permit a lipoaspirate fluid to enter the container above the bottom. In one embodiment the inlet is positioned in the upper half of the container, wherein the input port is sized and adapted for lateral delivery/injection (i.e., delivered in a direction generally parallel to the bottom if the bottom is flat and at roughly a 90 degree angle to the container wall; delivered in a direction so that lipoaspirate entering the container flow circumferentially) of entering lipoaspirate fluid onto the inner wall of the container. The method includes providing a source of a vacuum coupled to the container to provide a partial vacuum during use of the system. In addition, the method includes creating a partial vacuum within the container to pull fresh lipoaspirate particles through the input port so that the fresh lipoaspirate particles flowed circumferentially along the inner wall of the container.

DESCRIPTION OF ILLUSTRATIVE EMBODIMENTS

Figure 1A:
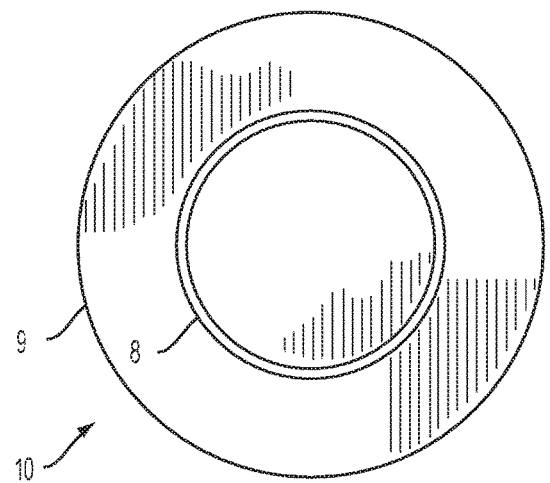
FIGS. 1a and 1b illustrate a slanted shelf 10 to be used in a canister. The shelf 10 can have a range of angles depending on flow rates and other variable. The shelf depicted is used in conjunction with a canister that is generally in the shape of a cylinder.

It is well-established that adipose tissue is an excellent source of stem cells compared to the more traditional bone marrow source. In one embodiment, the canister processes two liters under constant pressure of −18 mmHg and constant flow. In one configuration, the device includes a lid with inputs located for the vacuum and input flow. The negative pressure created by the vacuum will be used to force the flow of the lipoaspirate into the canister. In certain embodiments, a cone deflects the momentum of the flow of lipoaspirate, a shelf enables the collection of the higher density fat particles, and a mesh of 40 micron pores towards the bottom of the canister that filters out the liquid. The end of the canister also will contain an outlet port for the separation of the liquid without fat particles. An example of canister specifications is as follows: canister pressure, −18 mmHg; canister volume, 2 L; lid ports, 2 (vacuum, input flow); interior cone 9 cm diameter; interior shelf, 2 cm width; interior mesh filter, 40 micron pores.

One embodiment of this invention is a system that includes a fixed shelf that juts out from the interior canister wall for the purpose of retaining high-density tissue fragments as they fell and a central cone for the lateral deflection of introduced lipoaspirate. Placement of the shelf, in terms of clearance from the cone, was based on volume considerations relating the estimated fraction of sinking tissue fragments to the lipoaspirate volume and the total volume of the container itself. If contamination is to be minimized, the shelf must be able to hold all of the descending fragments. This means that a successful design will involve an optimized shelf width and may even need an angled shelf, lipped shelf, or multiple shelves if there are too many sinking tissue fragments. One issue that should be noted is that as the tissue enters the vessel, we do not expect the low and high density tissues to already be partitioned into discrete fractions. Rather, we understand that these variable-density tissues may be interspersed within each other. This means that, depending on the state of the entering tissues, low-density tissues that are interspersed with high-density pockets may also sediment to the shelf.

Another internal component of the initial canister is a cone used for momentum damping and deflection. This cone was supported by a pipe affixed to the bottom of the container which positioned the cone directly under the input valve. As lipoaspirate is introduced into the canister, the idea was that the cone would be able to direct fat and connective tissue to the shelf below, allowing fluid to fill the bottom of the vessel. The fluid level would rise until the fluid line eventually breached the bottom of the cone. At this point, one issue that could arise from a system with an unperforated cone would be the entrapment of air underneath the cone while the vacuum above and around the top of the cone creates a region of negative pressure. In order to avoid the mechanical instability that could result from the pressure gradient, the uppermost region of the cone was to be perforated with a series of holes, allowing the pressure inside and outside of the cone to equilibrate. Maintaining equal air pressure inside and outside of the cone would allow the fluid under the cone to fill normally and alleviates potential pressure-related stresses.

The device is designed to support a working volume of 1.6 liters which can be roughly broken down into 400 milliliters of Phosphate-buffered saline (PBS), which would be introduced to the canister prior to surgery, and 1.2 liters of lipoaspirate which would be introduced into the system at a rate dependent upon the vacuum pressure applied. This working volume would fill the inside of the canister from the outlet cover at the bottom of the device all the way up to roughly 1.5 cm from the top of the cone, which is reserved for air vents. As lipoaspirate is introduced, low density lipid particles are expected to sit atop the rising fluid level while higher density particles are expected to come to rest on the shelf. The shelf itself encircles the inner circumference of the canister and has a width of 2 cm, leaving the inner hole at 8 cm. The cone, which has a maximum diameter of 9 cm and is supported by a fixture from the bottom plate, sits 3 cm above the shelf and has a total height of 8.5 cm. As mentioned above, the topmost 1.5 cm of the cone will be perforated with air vents—these vents are covered by a domed vent shield to prevent clogging of the vents. The cap to our device has three inputs for surgical and operational accessibility.

Initial testing was done upon a system built with a flat shelf. That is, the shelf that is designed in order to catch the solid pieces of fat tissue was a solid plastic shelf that was parallel to the ground plane. This was the easiest solution to implement both theoretically and in a physical model.

A second shelf investigated was a slanted shelf. Much like the first design, this design included a shelving unit and, a momentum damping cone. While this second design concept included a solid plastic shelf, it was a different design in that instead of a flat shelf to catch the fat, the shelf was designed in a manner such that the inner diameter was higher than the outer diameter. This results in a slanted shelf that allows for the device to catch and hold the fat particles to a greater degree. The computer design and its physical realization can be seen in FIGS. 1 *a* and 1 *b*. This design is ultimately based upon a single shelf 10, with an inner diameter 8 and an outer diameter 9, that holds the dense fat while the relatively low density fat will still rise above on the shelf and flow over. The angle of the shelf can vary depending on the particular system being designed. This idea can be taken to the next step by having a second shelf which would catch the flow over and perform a similar separation.

While the slanted shelf may prove to be the right solution to the problem, it may have a few drawbacks. The main issue is that the shelf can fill with fluid and effectively become a flat shelf comprised of liquid. This could be overcome by creating a mesh shelf. This would be done by having a lead wire formed into two circles, an inner diameter and an outer diameter and having 3 struts to support the inner diameter from the outer diameter which is connected to the inner side of the canister. With correct positioning, this shelf could be built in the same manner as the slanted shelf mentioned in the previous paragraph, but would allow for liquid to flow through the shelf, leaving just the solid particles. This seems to be the optimum proposed solution to separation process via a shelf and cone system.

The inventors have determined that another issue with the system derives from the pulsatile nature of liposuction. Liposuction is not a continuous process; the removal of fat from the body and subsequent introduction into a primary vessel such as our own separation system is highly punctuated and any device expected to deal with such a process must be designed as such. We observed that pulsed vertical introduction was shooting the fluid into the canister with such velocity that the particles would merely flow around the cone before flowing straight downwards. In other words, contact with the cone alone was an insufficient retarding force and thus insufficient as a momentum dampener. In order to overcome this flaw in the system, the addition of a preintroductory expansion chamber has been envisioned. This chamber would be connected to the input valve before the canister so that the inflow could expand within an internal area greater than that of the tube. This would decrease the fluid velocity through the system because, assuming the volumetric flow rate is constant, an increase in internal area of the tube would drive a decrease in velocity (the two are inversely proportional). This concept is visualized in FIG. 2. The expansion chamber 20 (shown by dotted line 21) attaches to lid 40, which itself is coupled to canister 30.

Figure 2:
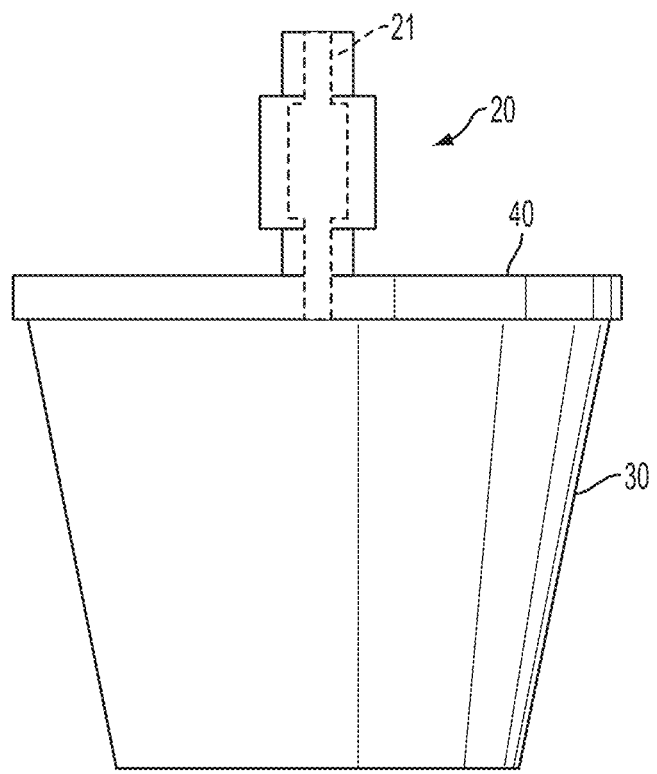
FIGS. 2 and 3 illustrate two embodiments of an expansion chamber 20. The expansion chamber shown in FIG. 3 has a sloped section 22 toward the bottom which permits gradual reduction in size back to the diameter of the inlet tube diameter above the expansion chamber.
Figure 3:
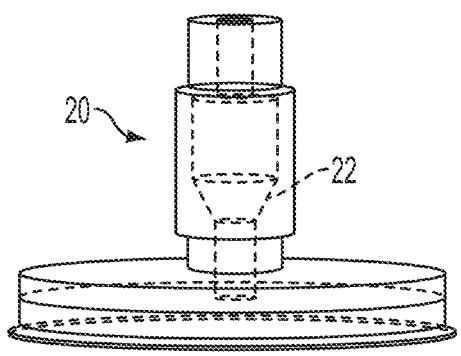

The inventors recognize that there may be issues that can arise from the Expansion Chamber concept. The first is the fact that if the camber is built as is shown in FIG. 2, the 90-degree angles at the bottom of the chamber could provide a location for fat tissue deposition. This could cause potential problems with clogging. This can be solved by changing the geometry such that the chamber gradually returns to the normal tube size. This change in geometry can be seen in FIG. 3 over the span of truncated cone 22. Also a system was envisioned such that the expansion chamber does not return to normal tube size, and introduces the fat mixture to the canister at the larger internal diameter.

Another possible and/or complementary strategy to solve the problem of high velocity introduction of lipoaspirate to the liposuction canister is the lateral introduction through a side inlet. Currently, it is believed that all commercially available liposuction canisters introduce lipoaspirate by means of a vertically-oriented lid inlet. Thus, all of the momentum is directed downward, resulting in a large negative z velocity that results in the liquid itself causing splashing and other harmful forces on the adipocytes and stem cells.

Introducing the lipoaspirate horizontally eliminates any initial z velocity; all of the kinetic energy is dedicated to motion in the horizontal plane. As the lipoaspirate swirls down and around the canister, the particles will accelerate slightly downwards. However, this gravitational effect is negligible. Ideally, it is desired that the lipoaspirate flow to hug the walls, losing momentum as the frictional shear forces applied by the wall slow the particles. This means in essence, that the frictional forces that are provided by the wall counter the gravitational forces, thus the x and y forces will slow down the negative z-plane momentum, and therefore will provide a safer, slower input method of the lipoaspirate.

Figure 4A:
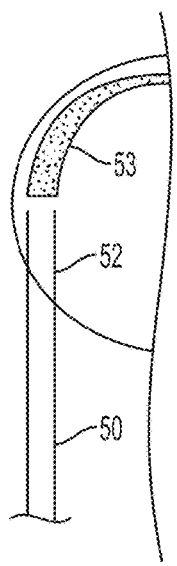
FIGS. 4a and 4b illustrate a generally cylindrical canister/container 30 that includes an inlet tube 50 positioned in the upper half, preferably the upper quarter, of the canister.
Figure 4B:
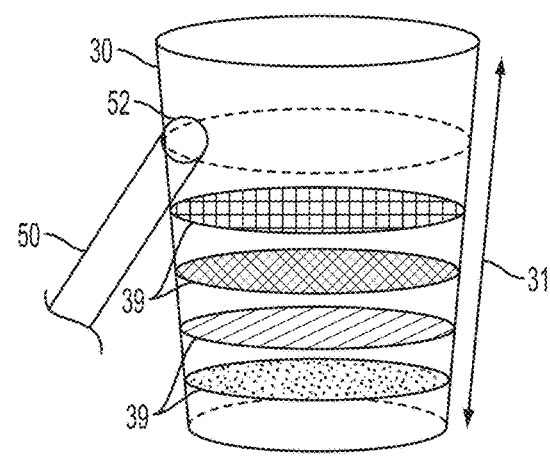

In this regard, FIGS. 4a and 4b illustrate this method of momentum disruption wherein the fluid inlet 50 to be directed into the side of the canister at an angle almost tangential to the cylindrical surface 31 of canister 30. A short portion 52 of the lipoaspirate-carrying tube is affixed to the inner wall of the canister to help directly flow along the inner wall. This introduction produces an initial flow that is lateral 53 and then swirls down.

Figure 5:
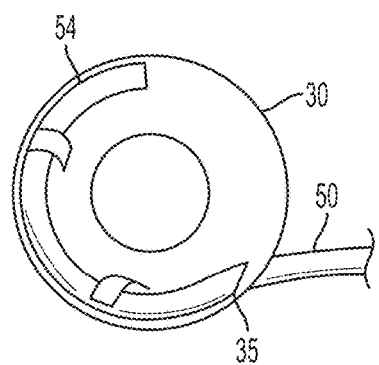
FIG. 5 illustrates an alternative inlet configuration in which a portion of tube 52 is affixed to the wall of the container so that the lipoaspirate enters the container laterally. The container can include one or more mesh shelves 39.

In our initial testing of the lateral input device, we affixed the incoming tube to the wall through a hole drilled in the commercially available canister. This tube provides the necessary tangential forces on the lipoaspirate that are need to send the fluid and solids in the x-y direction. However, in one embodiment such as shown in FIG. 5, a port 35 is positioned on the lateral part of the canister wall. This port will be connected to an internal tube 54 which will wrap along the inside of the canister wall, such as shown in FIG. 5, which is a top down view of a representative canister 30. The length of the internal tube can be optimized to provide the greatest tangential forces to direct the flow of the lipoaspirate along the wall, thus providing maximum frictional forces to slow down the material. This port can also have an input such that the surgeon will be able to connect the input lipoaspirate tube directly to the outside in the same manner as the industry standard top input connection.

Due to biohazard concerns and the difficulties associated with obtaining human lipoaspirate, we used a lipoaspirate substitute to conduct testing. We opted for fat taken from the dorsum of chickens. The isolated chicken fat was incubated at 37° C. for an hour to obtain a consistency similar to that of in-vivo fat. The fat was added to water, resulting in a mixture similar to the heterogeneous mixture that constitutes human lipoaspirate.

In experiments using the chicken fat substitute, one canister with a flat shelf and the other with an inclined shelf, connected to a vacuum source. We introduced a starting volume of water to represent the PBS solution used in the liposuction surgery. We had a tube connected to the input of the canister to input the fat mixture. The overall testing results can be seen below and the testing setup can be seen in FIG. 6 which shows canister 30, lid 40, inlet port and inlet tube 41, 50, and vacuum line 60.

Testing of Flat Shelf

Figure 6:
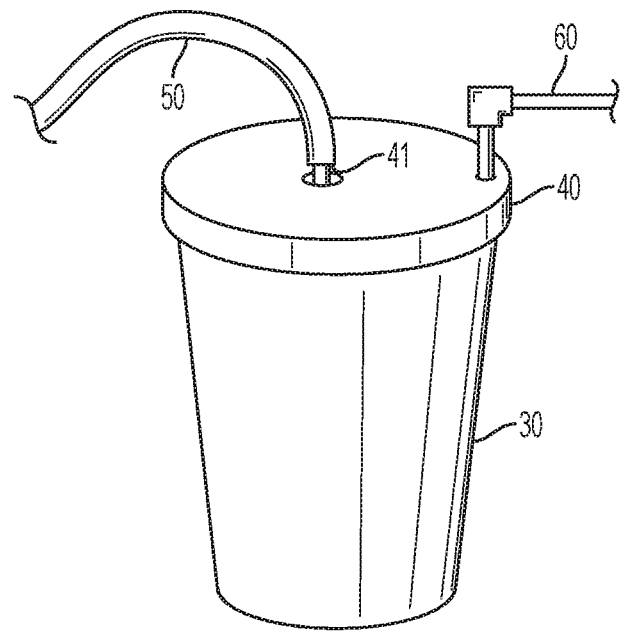
FIG. 6 illustrates an experimental set up with the inlet and vacuum source attached to the lid.
Figure 7:
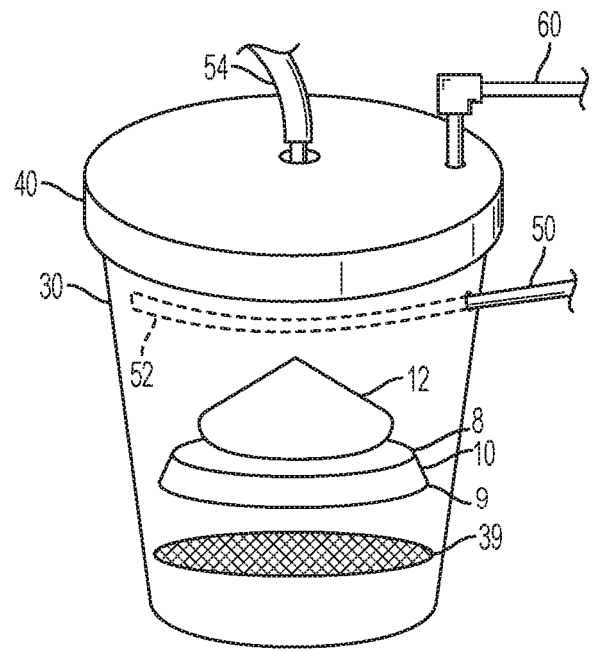
FIG. 7 illustrates an embodiment of the invention where a container 30 is fitted with a lid 40 that connects to vacuum source 60. The inlet tube 50 includes a section 52 affixed to the inner wall of the container to permit lateral introduction of fluid into the container 30. The system optionally includes a cone 12 that has an outer diameter greater than the inner opening diameter of the slanted shelf 10. Though depicted here, the cone 12 is typically used if the inlet is attached to the lid such that the lipoaspirates descends in a vertical direction from the lid through, for example, optional vertical inlet tube 54. The system includes on (truncated conical) slanted shelf 10 which catches lipoaspirate as described herein. The slanted shelf 10 includes an inner diameter 8 and an outer diameter 9. The system includes a mesh shelf 39 below the cone 10.

Empirical testing of the device involved the introduction of the blended chicken fat mixture into the separation canister as shown in FIG. 6. Using a handheld vacuum source, a negative pressure was applied to the inside of our canister, providing a driving force. To mimic the techniques used in clinical liposuction, where the surgeon pulses the vacuum to selectively remove undesired tissues, a pulsing technique was used to introduce the fat mixture into the canister. At the start, the system was able to intake the mixture of fluids and small pieces of fat without any problems. However, fat gradually began to accumulate, building up on the inside of the tube. Eventually, larger pieces of fat clogged the tubing completely, leading to small fractures and the eventual implosion of the canister.

The mechanical failure of the system led us to believe that tube blockage was responsible for the buildup of negative pressure within the canister. To solve this issue, we decided to grind up the chicken fat using a food processor to get smaller pieces. We estimated the extent of grinding that was necessary to obtain the consistency of a realistic human sample. Additionally, we also switched to a stronger wall vacuum source and changed the tube to a longer, more rigid tube which would allow larger fat particles to flow more smoothly. These changes were made to our second assembled canister, which was fitted with a flat plexiglass shelf. The introduction of the fat surrogate proceeded smoothly, but we were still unable to achieve our desired level of separation.

Testing of Inclined Shelf

After modifying our experimental setup, we decided to replace our original planar shelf with an inclined shelf capable of preventing lipoaspirate from slipping off our flat shelf. The second series of experiments was done using the same fat mixture and protocol but with an inclined shelf instead of a flat plexiglass shelf.

Despite the implemented inclined shelf, the solid fat particles did not seem to preferentially accumulate on the shelf. Each new pulse of fat mixture would displace the accumulated fat on the shelf. In this experiment only about 15% of the fat resides on top of the shelf and the composition of the top layer consist of mostly liquid.

3.3 Cone

Figure 1B:
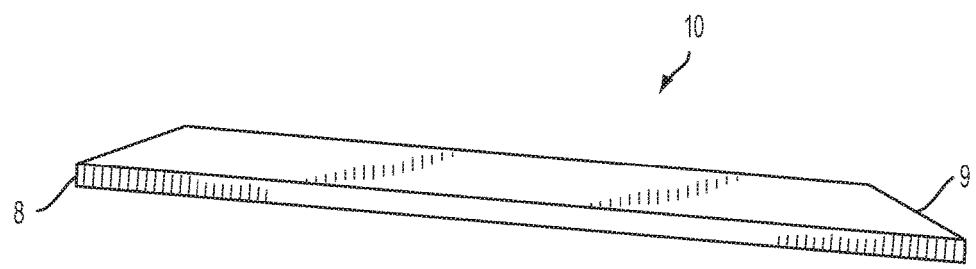

A cone attached to a polyvinyl chloride pipe was used to dissipate the momentum and to deflect the flow laterally. The first cone tested had a diameter barely larger than the inner opening of the plexiglass shelf. However, the first series of experiments showed that the cone did not provide sufficient deflection of the introduced fluid. We observed that a large proportion of the mixture flows directly downwards into the second compartment of the canister. That is, the relatively small size of the current cone allows for fluid and fat to bypass contact with the shelf altogether, undermining the objective of the shelf. To correct this issue, we decided to design and fabricate a larger cone such as depicted in FIGS. 1a and 1b.

We tested the lateral introduction system discussed above. The test was performed individually and on two of the meshes (those with pore diameters of 100 and 1000 microns) and the fluid was directed through a circular hole drilled into the side of the canister. The test was also performed collectively on four of the meshes (those with pore diameters of 36, 100, 1000, and 5000 microns) and the fluid was directed through a circular hole drilled into the side of the canister. The tube was threaded through the hole and attached along the edge of the wall to encourage flow along the wall (see FIG. 5). We observed circumferential flow, as expected, and the lipoaspirate surrogate particles were sufficiently slowed by the time they contacted the mesh. Meshes of both sizes were able to stop a reasonable fraction of the solid particles. The lateral introduction system provided improved separation, improved deceleration of the incoming particles, and improved results.

While the invention may be adaptable to various modifications and alternative forms, specific embodiments have been shown by way of example and described herein. The materials used to make the components such as the lid, container, slanted shelf, cone, inlet tube, and so on, are made of materials suitable for medical use. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed methods and systems may be utilized in various combinations and/or independently. Thus the invention is not limited to only those combinations shown herein, but rather may include other combinations.

REFERENCES

1. Zuk, Patricia. "Human Adipose Tissue Is a Source of Multipotent Stem Cells—Zuk Et Al. 13 (12): 4279." Molecular Biology of the Cell. MBoC, December 2002. Web. 3 Dec. 2010. <http://www.molbiolcell.org/cgi/content/short/13/12/4279>.
2. Gimble, Jeffery M., Adam J. Katz, and Bruce A. Bunnell. "Adipose-Derived Stem Cells for Regenerative Medicine." Circ. Res. 100 (2007): 1249-260. Print.
3. Romanov, Yu A., A. N. Darevskaya, N. V. Merzlikina, and L. B. Buravkova. "Mesenchymal Stem Cells from Human Bone Marrow and Adipose Tissue: Isolation, Characterization, and Differentiation." Cell Technologies in Biology and Medicine 3 (2005): 158-63. Print.
4. Strem, Brian M., Kevin C. Hicok, Min Zhu, Isabenna Wulur, Zeni Alfonso, Ronda E. Schreiber, John K. Fraser, and Marc H. Hedrick. "Multipotential Differentiation of Adipose Tissue-derived Stem Cells." Keio J Med 54.3 (2005): 132-41. Web.
5. AquaVage Fat Grafting Systems. Web 19 Nov. 2010. http://www.aquavage.com/
6. "Lipivage™ Fat Harvest, Wash, & Transfer Systems— Genesis Biosystems, Inc." GenesisBioSystems.com—Microderabrasion Equipment, Machines, System—Microdermabrasion Machine. Web 19 Nov. 2010. http://www.genesisbiosystems.com/lipivage-systems.html
7. "Triage." Cytori Therapeutics, Inc. Home. Web 19 Nov. 2010. http://www.cytori.com
8. Boschert, Mark T., Beckert Benjamin W., Puckett Charles L., Concannon, Mathew J., "Analysis of Lipocyte Viability after Liposuction." Plastic and Reconstructive Surgery. 109.2 (2002) 761-65. Print.
9. Wendt, J F. (1995). Computational fluid dynamics an introduction. Berlin: Springer-Verlag.
10. Zuk, Patricia A., Min Zhu, Peter Ashjian, Daniel A. De Ugarte, Jerry I. Huang, Hiroshi Mizuno, Zeni C. Alfonso, John K. Fraser, Prosper Benhaim, and Marc H. Hedrick. "Human Adipose Tissue Is a Source of Multipotent Stem Cells." Molecular Biology of the Cell 13 (2002): 4279-295. Print.

What is claimed is:

1. A system for isolating and separating lipoaspirate particles, comprising:
a generally cylindrical container having a lid and a bottom wherein the generally cylindrical container includes an input port positioned to permit a lipoaspirate fluid to enter the generally cylindrical container above the bottom and a shelf fixed to a wall of the generally cylindrical container between the input port and the bottom, wherein the input port is directed into a side of the generally cylindrical container with a central axis of the input port oriented at an angle that is almost tangential to the side of the generally cylindrical container where the input port enters the generally cylindrical container, wherein the shelf comprises an open central portion, and wherein the shelf is slanted such that an inner diameter of the shelf is disposed at a higher elevation than an outer diameter of the shelf;
a source of a vacuum coupled to the generally cylindrical container to provide a partial vacuum during use of the system; and
an expansion chamber coupled to the input port.

2. The system of claim 1, including at least one exit port in the generally cylindrical container for removing separated lipoaspirate fluid.

3. The system of claim 1, including at least one mesh shelf in the generally cylindrical container below the shelf.

4. The system of claim 1, wherein the input port is positioned in an upper half of the generally cylindrical container.

5. A method of separating lipoaspirate particles, comprising:
providing a cylindrical container having a lid and a bottom wherein the cylindrical container includes at least one input port positioned to permit a lipoaspirate fluid to enter the cylindrical container above the bottom, wherein the input port is directed into a side of the cylindrical container with a central axis of the input port oriented at an angle that is almost tangential to the side of the cylindrical container where the input port enters the cylindrical container, and wherein the cylindrical container includes a shelf fixed to a wall of the cylindrical container, the shelf having an open central portion, and wherein the shelf is slanted such that an diameter part of the shelf is disposed at a higher elevation than an outer diameter of the shelf;
providing a source of a vacuum coupled to the cylindrical container to provide a partial vacuum during use of the cylindrical container;
creating a partial vacuum within the cylindrical container to pull fresh lipoaspirate particles through the input port so that the fresh lipoaspirate particles flows into the cylindrical container; and
wherein the cylindrical container further comprises an expansion chamber coupled to the input port.

6. The method of claim 5, including wherein the cylindrical container includes at least one exit port in the cylindrical container for removing separated lipoaspirate fluid.

7. The method of claim 5, wherein the cylindrical container includes at least one mesh shelf in the cylindrical container below the shelf.

8. The method of claim 5, wherein the input port is positioned in an upper half of the cylindrical container.

9. The method of claim 5, wherein the input port comprises a tube affixed to an inner wall of the cylindrical container for lateral delivery/injection of entering lipoaspirate fluid onto the inner wall of the cylindrical container.

10. A system for isolating and separating lipoaspirate particles comprising:

a generally cylindrical container having a lid and a bottom wherein the generally cylindrical container includes at least one input port positioned to permit a lipoaspirate fluid to enter the generally cylindrical container above the bottom;

a cone disposed within the generally cylindrical container, the cone comprising a tip pointing up toward the input port;

a ring-shaped shelf fixed to a wall of the generally cylindrical container and disposed between the cone and the bottom of the generally cylindrical container, the ring-shaped shelf comprising an inner diameter defining an open central portion and an outer diameter that is greater than the inner diameter;

a source of a vacuum coupled to the generally cylindrical container to provide a partial vacuum during use of the system; and an expansion chamber coupled to the input port.

11. The system of claim 10, wherein a relative height of the inner diameter of the ring-shaped shelf is higher than the outer diameter of the ring-shaped shelf.

12. The system of claim 10, including at least one mesh shelf in the generally cylindrical container below the ring-shaped shelf.

13. The system of claim 10, wherein a bottom diameter of the cone is larger than the inner diameter of the ring-shaped shelf.

14. The system of claim 10, wherein the cone comprises perforations to permit equalization of pressure between an area of the generally cylindrical container beneath the cone with an area of the generally cylindrical container above the cone.

* * * * *